(12) United States Patent
Martin et al.

(10) Patent No.: US 8,409,204 B2
(45) Date of Patent: Apr. 2, 2013

(54) SURGICAL METHOD FOR REPAIRING A FRACTURED SHOULDER JOINT

(75) Inventors: Jean-Jacques Martin, Bourg en Bresse (FR); Tristan Lascar, Cap d'Ail (FR); Laurent Obert, Vorges les Pins (FR)

(73) Assignee: Compagnie Financiere et Medicale SARL (FR)

( * ) Notice: Subject to any disclaimer, the term of this patent is extended or adjusted under 35 U.S.C. 154(b) by 29 days.

(21) Appl. No.: 13/239,438

(22) Filed: Sep. 22, 2011

(65) Prior Publication Data

US 2012/0089143 A1  Apr. 12, 2012

Related U.S. Application Data

(60) Provisional application No. 61/392,050, filed on Oct. 12, 2010.

(51) Int. Cl.
*A61B 17/56* (2006.01)
(52) U.S. Cl. ............ 606/62; 623/19.11; 623/19.14
(58) Field of Classification Search .......... 606/62–64; 623/19.11–19.14
See application file for complete search history.

(56) References Cited

U.S. PATENT DOCUMENTS

| | | | |
|---|---|---|---|
| 6,334,874 B1* | 1/2002 | Tornier et al. | 623/19.14 |
| 2005/0177241 A1* | 8/2005 | Angibaud et al. | 623/19.14 |
| 2009/0265010 A1* | 10/2009 | Angibaud et al. | 623/19.11 |
| 2010/0076561 A1* | 3/2010 | Emmanuel | 623/19.11 |

FOREIGN PATENT DOCUMENTS

FR 2939639 6/2010

* cited by examiner

*Primary Examiner* — Eduardo C Robert
*Assistant Examiner* — Nicholas Plionis
(74) *Attorney, Agent, or Firm* — Defillo & Associates, Inc.; Evelyn A Defillo

(57) ABSTRACT

This method comprises the use of a repair equipment including a humeral rod (2) intended to be placed in the medullary cavity of the humerus, comprising at least one hole (6) for receiving a thread (11) for repositioning the tuberosities (101, 102) and for maintaining the latter with respect to the rest of the bone. Said hole (6) is formed in the metaphyseal portion of the humeral rod (2), in the anteroposterior direction thereof; and the repair equipment further comprises a so-called "guying" subassembly (3), to maintain the tuberosities (101, 102) when they re-installed, two second so-called "traction" subassemblies (4), for pulling of the tuberosities (101, 102) one toward the other, and two so-called third "pressing" subassemblies (5), for tackling the tuberosities (101, 102); each of these sub-assemblies comprises a needle and thread (11) connected to this needle, this thread (11) forming a loop.

8 Claims, 5 Drawing Sheets

SURGICAL METHOD FOR REPAIRING A FRACTURED SHOULDER JOINT

CROSS-REFERENCE TO RELATED APPLICATIONS

This application claims the benefit of priority to U.S. Provisional Application No. 61/392,050 filed Oct. 12, 2010, the contents of which are incorporated herein by reference.

BACKGROUND OF THE INVENTION

The present invention relates to a surgical method for repairing a fractured shoulder joint.

It is well known to repair a shoulder joint using a shoulder prosthesis comprising a humeral rod intended to be inserted into the medullary cavity of the humerus. This rod can receive a condyle (which can be either the reimplanted native bone head or a prosthetic head); in the case of a prosthetic head, the prosthesis also comprises a portion implanted on the shoulder blade, forming a corresponding glenoid.

A fractured shoulder joint frequently involves a fracture of the tuberosities (lesser and greater tuberosities of the humerus), which must consequently be replaced on the prosthesis in precise and stable positions. Failing this, the obtained ligamentary and muscular tensions are not optimal, which noticeably affects the operation of the restored joint.

To replace the tuberosities, it is known to provide a fin protruding on the outer side of the humeral rod, pierced with holes intended to receive metal wires for maintaining said tuberosities once they are put back into place. These wires are intended to surround the tuberosities and to be twisted to keep the latter in position.

This technique is not completely satisfactory, as it can lead to relatively imprecise repositioning of the tuberosities and insufficient immobilization thereof relative to the rest of the bone, affecting the consolidation of the latter.

The present invention aims to resolve this essential drawback.

BRIEF DESCRIPTION OF THE INVENTION

The invention relates to a surgical method comprising the following steps:

using repair equipment comprising:

a humeral rod comprising at least one hole formed in its metaphyseal portion, in the anteroposterior direction thereof;

a first so-called "guying" subassembly, two second so-called "traction" subassemblies, and two so-called third "pressing" subassemblies, each of these subassemblies comprising a needle and a thread connected to said needle, this thread forming a loop, i.e. comprising two strands connected to the needle by first ends and connected to each other by second ends, opposite the first ends;

connecting the thread of the guying subassembly to the humeral diaphysis;

placing the humeral rod in the medullary cavity of the humerus;

engaging the thread of a first traction subassembly through the lesser tuberosity of the humerus and/or tendon of the subscapularis muscle, allowing part of the loop formed by said thread to protrude from the lesser tuberosity of the humerus and/or said tendon, and making said thread exit through the lesser tuberosity of the humerus, then engaging the thread in the protruding portion of the loop so as to form a choker knot with said loop;

engaging the thread of the second traction subassembly through the greater tuberosity of the humerus and/or the tendon of the supraspinous muscle, allowing part of the loop formed by said thread to protrude from the greater tuberosity of the humerus and/or said tendon, and making said thread exit through the greater tuberosity of the humerus, then engaging the thread in the protruding portion of the loop so as to form a choker knot with said loop;

engaging the thread of a first pressing subassembly through the tendon of the subscapularis muscle, allowing part of the loop formed by said thread to protrude from said tendon, then engaging said thread through the hole in the humeral rod, making it pass around said humeral rod, making it exit through the lesser tuberosity of the humerus and engaging the thread in said protruding portion of the loop so as to form a choker knot with said loop;

engaging the thread of the second pressing subassembly through the tendon of the supraspinous muscle, allowing part of the loop formed by said thread to protrude from the tendon, then engaging the thread through the hole of the humeral rod, making it pass around said humeral rod, making it exit through the greater tuberosity of the humerus and engaging the thread in said protruding portion of the loop so as to form a choker knot with said loop;

while the joint is in neutral rotation, or external rotation, applying the tuberosities on the humeral rod without blocking them; then pulling on the threads of said traction subassemblies so as to tighten the aforementioned choker knots and obtain a balance of the muscle tensions produced by the subscapularis muscle and the infraspinatus/supraspinous muscle, then knotting said threads together while preserving that balance; a traction of the tuberosities toward each other is thus achieved;

stretching the threads of the pressing subassemblies so as to tighten the aforementioned choker knots, then knotting the thread of the first pressing subassembly to the thread of the second traction subassembly, and knotting the thread of the second pressing subassembly to the thread of the first traction subassembly; the tuberosities are thus pressed against the rest of the back;

engaging the thread of the guying subassembly through the tendon of the subscapularis muscle from the outside in, and through the tendon of the supraspinous muscle, from the inside out, then stretching that thread and knotting it with itself; strengthened guying of the reconstituted bone 100 is thus achieved.

The invention consequently provides a surgical method for repairing a fractured shoulder joint, consisting of combining (i) a humeral rod comprising an anteroposterior hole formed in its metaphyseal portion, and (ii) five subassemblies with needle and thread forming loops; this assembly making it possible to perfectly:

bring the two tuberosities closer to each other owing to the traction threads, repositioning them according to the muscle balance of the joint, press these tuberosities against the rest of the bone owing to the pressing threads passing through the humeral rod and therefore bearing against it, and immobilize the bone thus reconstituted owing to the guying thread completing the maintenance ensured by the traction threads and pressing threads.

As a result, the assembly according to the invention enables precise repositioning of the tuberosities and complete immobilization thereof relative to the rest of the bone, favorable to the consolidation of the entire bone.

Preferably, the method comprises the use of threads of different colors from one type of subassembly to the next, i.e.

for the thread of said guying subassembly, the threads of said two traction subassemblies and the threads of said two pressing subassemblies, for example green for the guying subassembly, yellow for the threads of the two traction subassemblies and blue for the threads of the two pressing subassemblies.

The different threads can thus be perfectly distinguished from one another during the various operations carried out.

The two strands of each thread may be formed by two separate thread portions, connected at said second ends using any means, in particular by knotting; preferably, however, the two strands are formed by a single and same thread, the connection of which at said second ends is simply done by the continuation of that thread.

The needles of the different subassemblies can in particular be curved.

This curvature favors the engaging of a thread in holes formed for its passage through the bone wall, in particular through the humeral diaphysis for connecting the guying thread thereto or through the lesser tuberosity of the humerus or the greater tuberosity of the humerus to connect the traction and pressing threads thereto.

The connection of a thread from a guying, traction and/or pressing subassembly to the corresponding needle is preferably done by stamping, on the thread, a deformable wall comprised by the end of the needle intended to be connected to said thread.

A perfect connection of the needle to the thread is thus obtained, as well as a continuation of the wall of the needle with the thread.

The repair method according to the invention can also comprise the use of a third traction subassembly, the thread of which can be placed through the greater tuberosity of the humerus and/or the tendon of the supraspinous muscle, using a choker knot as previously mentioned.

This third traction subassembly can be used if the greater tuberosity of the humerus is in two pieces.

The repair method according to the invention can also comprise a second guying subassembly, the thread of which can be engaged through the tendon of the supraspinous muscle, from the outside in, and through the tendon of the infraspinatus muscle, from the inside out, and can be knotted with itself.

An additional guying can thus be produced.

The step of the surgical method consisting of connecting the thread of the guying subassembly to the humeral diaphysis preferably comprises the following operations:

piercing two holes in the humeral diaphysis pulled back from the fracture area of the tuberosities;

engaging the thread of the guying subassembly through a first of these holes, from the outside toward the inside of the bone, then in the second hole, from the inside toward the outside of the bone.

The fastening of the thread of the guying subassembly to the humeral diaphysis is thus done simply.

The invention will be well understood, and other features and advantages thereof will appear, in reference to the appended diagrammatic drawing, showing, as a non-limiting example, one preferred embodiment of the repair equipment it concerns.

DETAILED DESCRIPTION OF THE INVENTION

Figure 1:
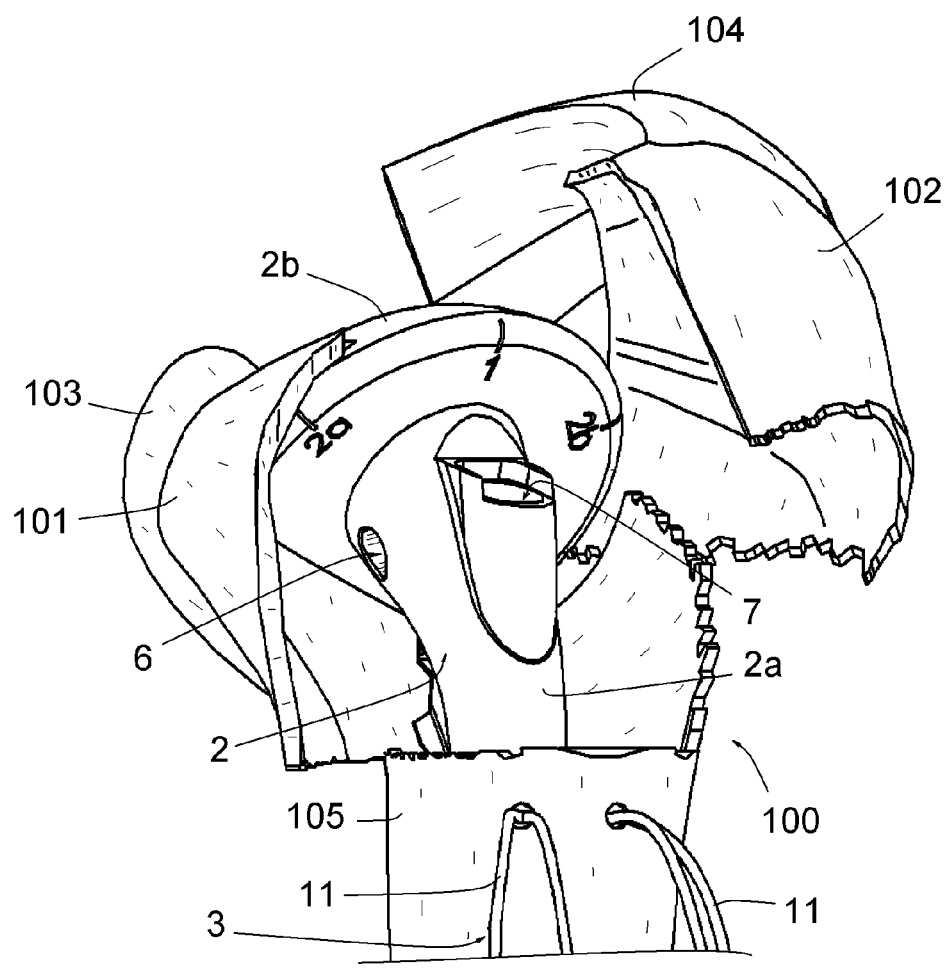
FIG. 1 is a perspective view of a humeral rod and the thread of a first needle and looped thread subassembly comprised by said repair equipment, this rod and thread being placed on the fractured upper end of a humerus.

FIGS. 1 and 3 to 10 show the upper end of a fractured humerus 100, whereof the tuberosities (lesser 101 and greater 102 tuberosity of the humerus) are fractured and completely or partially separated from the rest of the bone. References 103 and 104 respectively designate the tendons of the subscapularis muscle, connected to the lesser tuberosity of the humerus 101, and the supraspinous muscle, connected to the greater tuberosity of the humerus 102.

The repair equipment comprises a humeral rod 2 and three types of subassemblies 3, 4, 5 with a needle and a looped thread.

The surgical method allowed by this equipment comprises steps for placing the humeral rod 2 and the assemblies 3, 4, 5 on the bone, described in reference to FIGS. 1 and 3 to 5 below; it then comprises steps for knotting the threads of the assemblies 4, 5, and placing and knotting the assembly 3, described in reference to FIGS. 6 to 10 below.

FIG. 1 shows that the humeral rod 2 is intended to be placed on the humerus 100 by introducing a slender body 2a it comprises into the medullary cavity of the humerus. This rod 2 also comprises a protruding neck intended to receive a condyle 2b (this is a prosthetic head in the illustrated example, but could be the reimplanted native bone head). In this same illustrated example, the condyle 2b is indexable and comprises marks "1," "2a," "2b" indicating references for different possible positions of said head 2b relative to the rod 2a. This indexing possibility is a known feature and is therefore not described in detail.

The metaphyseal part of the slender body 2a comprises a hole 6 passing all the way through it, which emerges on the sides of said body 2a intended to be located respectively on the forward side and the rear side of the patient after implantation. The direction of this hole 6 is therefore anteroposterior after placement of the humeral rod 2 on the bone. This hole 6 can receive the two threads of the two third subassemblies 5, as visible in FIG. 5.

The slender body 2a also comprises a proximal impaction hole 7, this feature being known in itself.

The three types of needle and looped thread subassemblies 3, 4, 5 are broken down as follows:

a first so-called "guying" subassembly 3, two second so-called "traction" subassemblies 4, and two third so-called "pressing" subassemblies 5.

Figure 2:
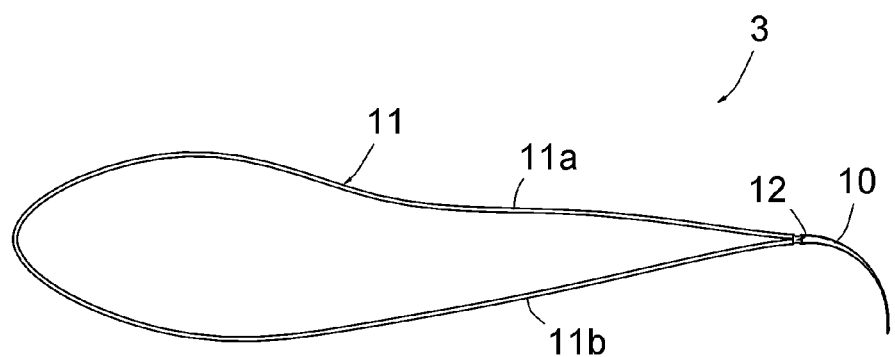
FIG. 2 is a planar view of said first subassembly.
Figure 3:
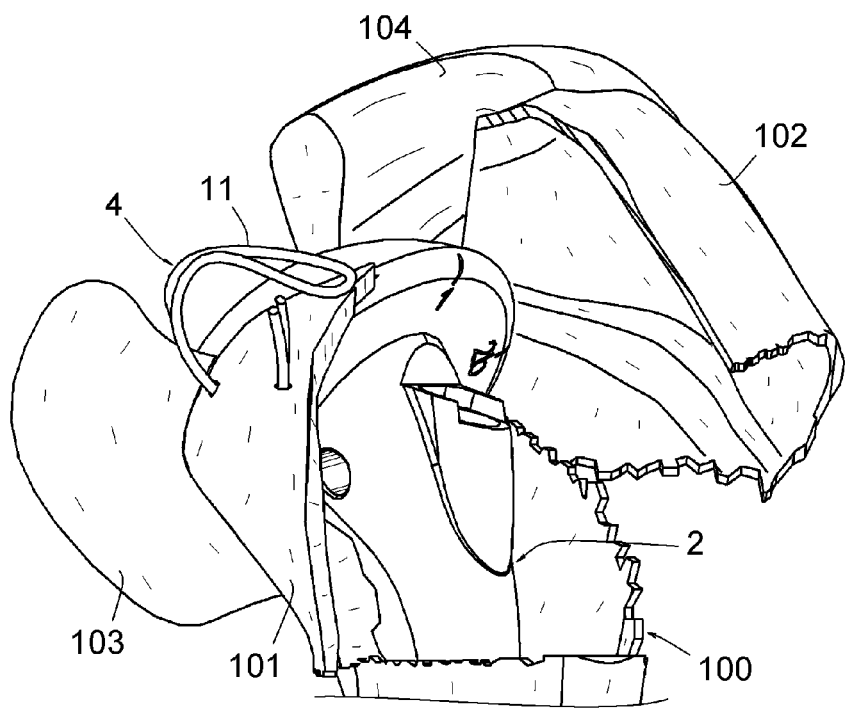
FIGS. 3 and 4 are perspective views of the upper end of the humerus, during the placement of two subassemblies also comprised by the repair material.

Each of these subassemblies 3, 4, 5 has the same structure, visible in FIG. 2 for subassembly 3, i.e. comprising a curved needle 10 and a thread 11 connected to said needle 10.

This connection of the thread 11 to the needle 10 is done by stamping, the needle 10 comprising a cavity for receiving the ends of the thread 11, defined by a deformable wall 12. Said wall 12 is, after engagement of those ends in said cavity, deformed on said ends.

The thread 11 thus forms a loop, i.e. comprises two strands 11a connected to the needle 10 on the one hand, by first ends, and connected to each other by second ends, opposite the first ends, said connection resulting simply from the continuation of said thread 11.

Figure 8:
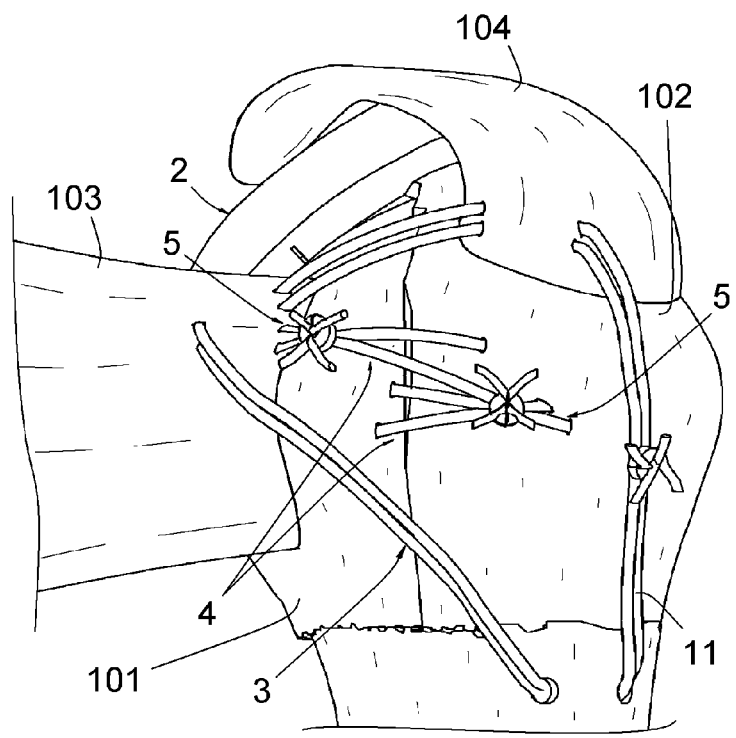
FIG. 8 is a perspective view of the upper end of the humerus, after engagement and knotting of the thread of the first subassembly.

The thread of the guying subassembly 3 is green. It has a length so that it can be connected to the humeral diaphysis 105 and can be engaged, when the tuberosities 101, 102 are put back into place, through the tendon 103 of the subscapularis muscle, from the outside in, and through the tendon 104 of the supraspinous muscle, from the inside out, then knotted with itself, as shown in FIG. 8.

As understood in reference to FIG. 1, the connection of the thread 11 of the guying subassembly 3 to the humeral diaphysis 105 is done by piercing two holes in said humeral diaphysis 105 pulled back from the fracture area of the tuberosities, then engaging the thread 11 through a first of said holes, from the outside toward the inside of the bone, then in the second hole, from the inside toward the outside of the bone.

The thread 11 of the first traction subassembly 4 is yellow. It has a length so that it can be engaged through the lesser tuberosity of the humerus 101 and/or the tendon 103 of the subscapularis muscle, allowing a part of the loop it forms to protrude from the lesser tuberosity of the humerus and/or the tendon, and to exit through the lesser tuberosity of the humerus (cf. FIG. 3), then can be engaged in said protruding portion of the loop so as to form a choker knot with said loop; said thread 11 can also be knotted to the thread 11 of the second traction subassembly 4 and the thread 11 of the second pressing subassembly 5 (cf. FIG. 7).

The thread 11 of the second traction subassembly 4 is also yellow. It has a length so that it can be engaged through the greater tuberosity of the humerus 102 and/or the tendon 104 of the supraspinous muscle, while allowing a portion of the loop it forms to protrude from the greater tuberosity of the humerus and/or said tendon, and can exit through the greater tuberosity of the humerus (cf. FIG. 4), then be engaged in said protruding portion of said loop so as to form a choker knot with said loop; the thread 11 can also be knotted to the thread of the first traction subassembly 4 and the thread of the first pressing subassembly 5 (cf. FIG. 7).

The thread 11 of a first pressing subassembly 5 has a length so that it can be engaged through the tendon 103 of the subscapularis muscle, allowing a portion of the loop it forms to protrude from said tendon, then through the hole 6 of the humeral rod 2, to pass around said humeral rod, exit through the lesser tuberosity of the humerus 101 (cf. FIG. 5) and be engaged in said protruding portion of the loop so as to form a choker knot with said loop; said thread 11 also has a length so that it can be knotted to the thread of the second traction subassembly 4.

The thread 11 of the second pressing subassembly 5 has a length so that it can be engaged through the tendon 104 of the supraspinous muscle, allowing a portion of the loop it forms to protrude from said tendon, then through the hole 6 of the humeral rod 2, pass around said humeral rod, exit through the greater tuberosity of the humerus 102 (cf. FIG. 5) and be engaged in said protruding portion of the loop so as to form a choker knot with said loop; said thread 11 also has a length so that it can be knotted to the thread of the first traction subassembly 4.

Figure 4:
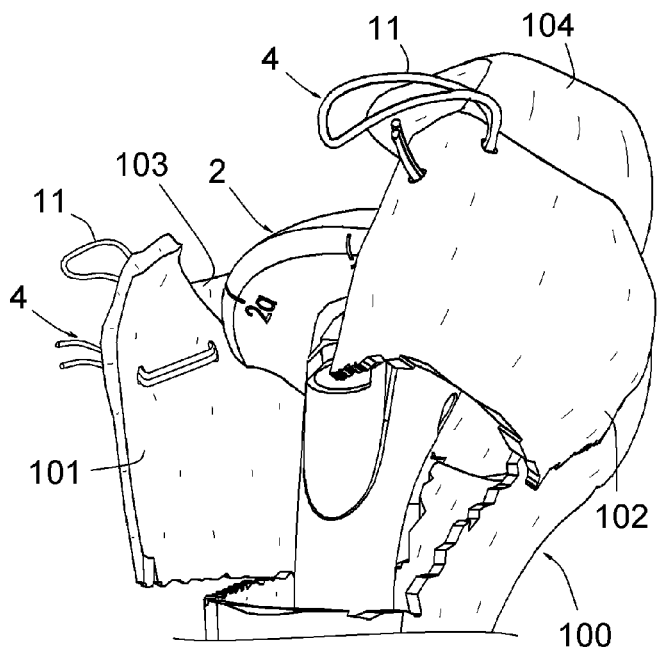
Figure 5:
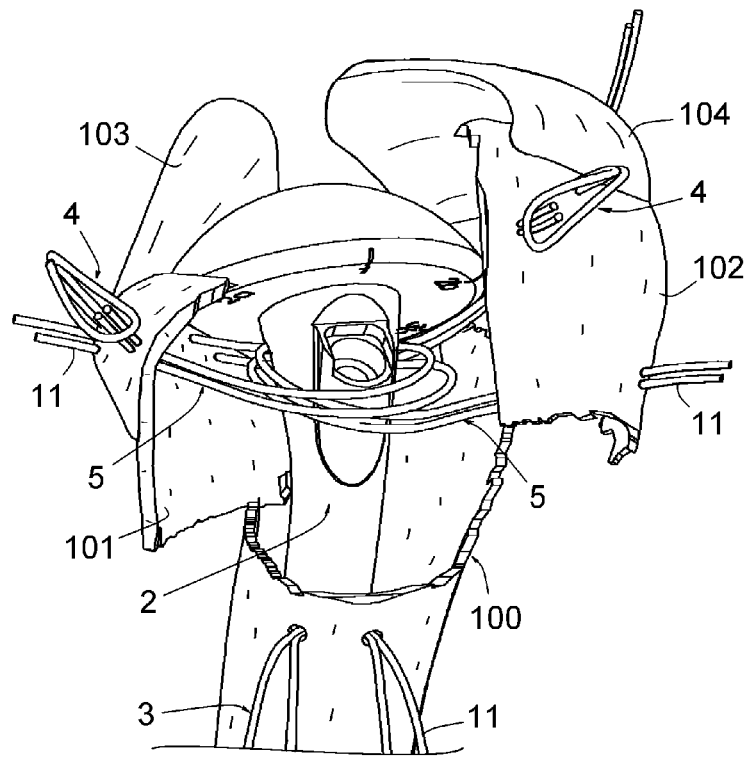
FIG. 5 is a perspective view of the upper end of the humerus, during the placement of two third subassemblies also comprised by the repair material.
Figure 6:
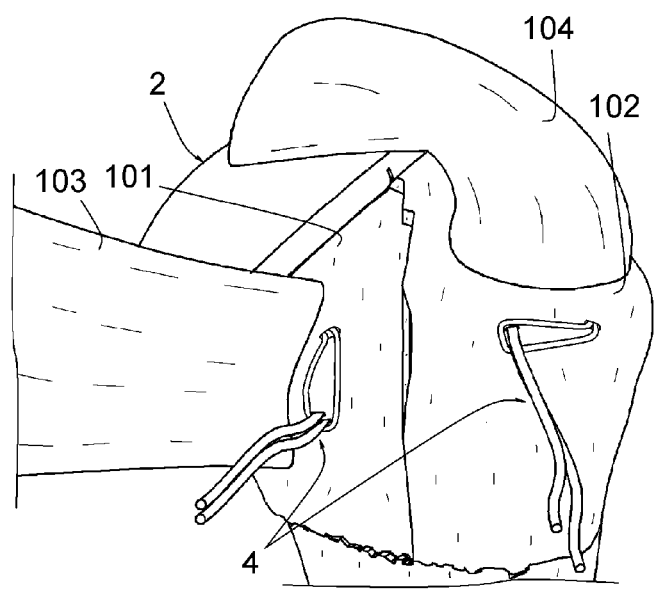
FIG. 6 is a perspective view of the upper end of the humerus, during the repositioning of the fractured tuberosities.

The aforementioned steps for placing the humeral rod 2 and the assemblies 3, 4, 5 on the bone consequently consist of:

connecting the thread (11) of the guying subassembly 3 to the humeral diaphysis and placing the humeral rod (2) in the medullary cavity of the humerus 100 (cf. FIG. 1);

placing the first traction subassembly 4 (cf. FIG. 3) and the second traction subassembly 4 (cf. FIG. 4);

placing the first and second pressing subassemblies 5 (cf. FIG. 5).

At that stage, the repair equipment assembly, as shown in said FIG. 5, is placed on the humerus 100.

Figure 7:
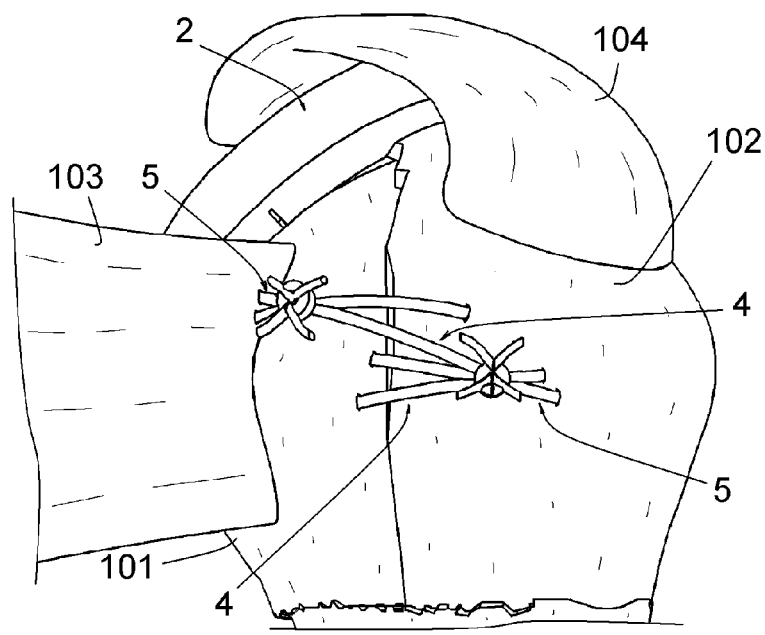
FIG. 7 is a perspective view of the upper end of the humerus, after knotting the threads of said second and third subassemblies to each other.

The steps for knotting the threads of the assemblies 4, 5 and placing and knotting the assembly 3 then consist of:

while the joint is in neutral rotation, or external rotation, applying the tuberosities 101, 102 on the humeral rod 2 without blocking them (cf. FIG. 6); then pulling on the threads 11 of said traction subassemblies 4 so as to tighten the aforementioned choker knots and obtain a balance of the muscular tensions produced by the subscapularis muscle and the infraspinatus/supraspinous muscle (cf. FIG. 6), then knotting said threads 11 to each other while preserving that balance; traction is then exerted on the tuberosities 101, 102 toward each other;

stretching the threads 11 of the pressing subassemblies 5 so as to tighten the aforementioned choker knots, then knotting the thread of the first pressing subassembly 5 to the thread of the second traction subassembly 4, and knotting the thread of the second pressing subassembly 5 to the thread of the first traction subassembly 4, cf. FIG. 7 (in FIG. 7, the loops of the choker knots of the subassemblies 4 are not shown for clarity reasons); the tuberosities 101, 102 are thus pressed against the rest of the bone 100;

engaging the thread 11 of the guying subassembly 3 through the tendon 103 of the subscapularis muscle, from the outside in, and through the tendon 104 of the supraspinous muscle, from the inside out, then stretching said thread 11 and knotting it with itself (cf. FIG. 8); a strengthening guying is thus produced for the reconstituted bone 100.

Figure 9:
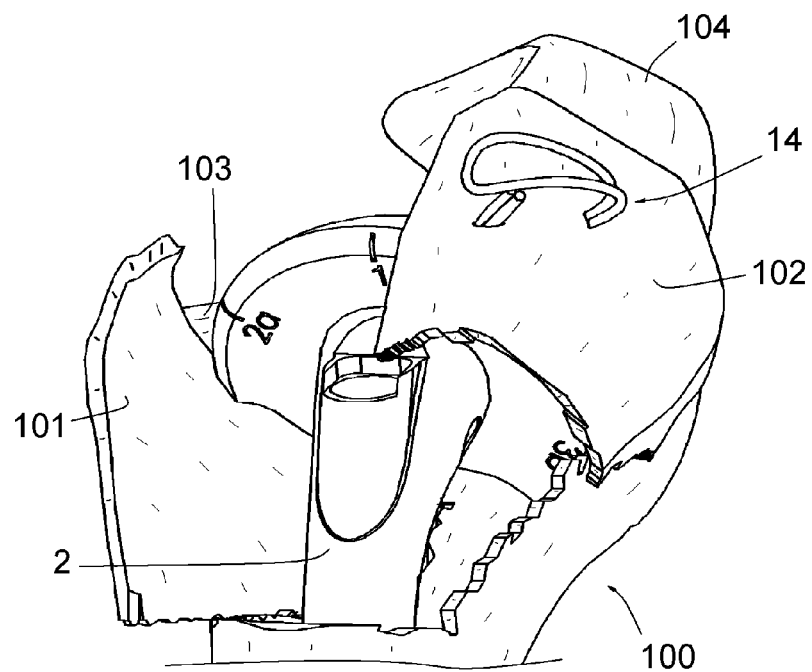
FIG. 9 is a perspective view of the upper end of the humerus, during the placement of an additional subassembly.

The repair equipment according to the invention can also comprise a third traction subassembly 14, the thread of which, still another color, for example white, can be placed through the greater tuberosity of the humerus 102 and/or the tendon 104 of the infraspinatus muscle, using a choker knot as previously mentioned (cf. FIG. 9). This third traction subassembly 14 can be used if the greater tuberosity of the humerus 102 is in two pieces.

Figure 10:
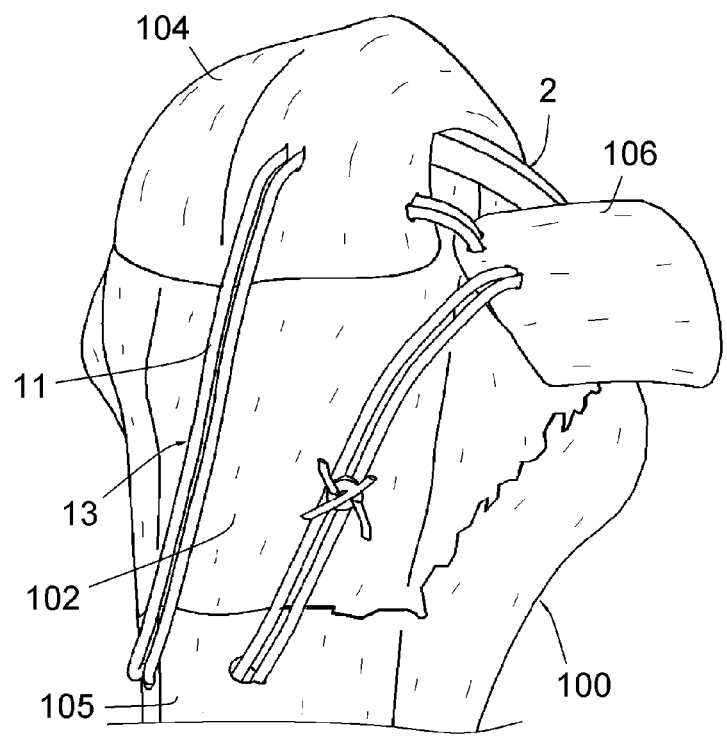
FIG. 10 is a perspective view of the upper end of the humerus, during placement of another additional subassembly.

The repair equipment according to the invention can also comprise a second guying subassembly 13, the thread 11 of which can be engaged through the tendon 104 of the supraspinous muscle, from the outside in, and through the tendon 106 of the infraspinatus muscle, from the inside out, and can be knotted with itself (cf. FIG. 10). An additional guying is thus produced.

As appears from the preceding, the invention provides a surgical method for repairing a fractured shoulder joint, consisting of combining (i) a humeral rod 2 comprising an antero-posterior hole 6 formed in its metaphyseal portion, and (ii) essentially five subassemblies 3, 4, 5 with needles 10 and threads 11 forming loops; said assembly makes it possible to perfectly:

bring the two tuberosities 101, 102 closer to each other owing to the traction threads, repositioning them according to the muscle balance of the joint, press these tuberosities 101, 102 against the rest of the bone owing to the pressing threads 11 passing through the humeral rod 2 and therefore bearing against it, and immobilize the bone thus reconstituted owing to the guying thread 11 completing the maintenance ensured by the traction threads 11 and pressing threads 11.

As a result, the assembly according to the invention makes it possible to precisely reposition the tuberosities and completely immobilize them relative to the rest of the bone, which is favorable to the consolidation of the entire bone.

The invention has been described above in reference to one embodiment provided as an example. It is of course not limited to that embodiment, but encompasses all embodiments covered by the appended claims.

What is claimed is:

1. A surgical method for repairing a fractured shoulder joint, comprising the following steps:
   a) using repair equipment comprising: a humeral rod comprising at least one hole formed in a metaphyseal portion in an anteroposterior direction thereof; a guying subassembly, two traction subassemblies, and two pressing subassemblies, each of these subassemblies comprising a needle and a thread connected to said needle, the thread forming a loop comprising two strands connected to the needle at first ends and connected to each other at second ends, opposite the first ends;
   b) connecting the thread of the guying subassembly to a humeral diaphysis of a fractured shoulder joint;
   c) placing the humeral rod in a medullary cavity of a humerus of the joint;
   d) engaging the thread of a first traction subassembly through at least one of a lesser tuberosity of the humerus and a tendon of a subscapularis muscle, allowing part of the loop formed by said thread to protrude from the at least one of the lesser tuberosity of the humerus and said tendon, and making said thread exit through the lesser tuberosity of the humerus, then engaging the thread in a protruding portion of the loop so as to form a choker knot with said loop;
   e) engaging the thread of a second traction subassembly through at least one of a greater tuberosity of the humerus and a tendon of a supraspinatus muscle, allowing part of the loop formed by said thread to protrude from the at least one of the greater tuberosity of the humerus and said tendon, and making said thread exit through the greater tuberosity of the humerus, then engaging the thread in the protruding portion of the loop so as to form a choker knot with said loop;
   f) engaging the thread of a first pressing subassembly through the tendon of the subscapularis muscle, allowing part of the loop formed by said thread to protrude from said tendon, then engaging said thread through the hole in the humeral rod, making it pass around said humeral rod, making it exit through the lesser tuberosity of the humerus and engaging the thread in said protruding portion of the loop so as to form a choker knot with said loop;
   g) engaging the thread of a second pressing subassembly through the tendon of the supraspinatus muscle, allowing part of the loop formed by said thread to protrude from the tendon, then engaging the thread through the hole of the humeral rod, making it pass around said humeral rod, making it exit through the greater tuberosity of the humerus and engaging the thread in said protruding portion of the loop so as to form a choker knot with said loop;
   h) while the joint is in a neutral rotation or an external rotation, contacting the greater and lesser tuberosities on the humeral rod without fixing thereto; then pulling on the threads of said traction subassemblies so as to tighten the aforementioned choker knots and obtain a balance of the muscle tensions produced by the subscapularis muscle, the supraspinatus muscle, and an infraspinatus muscle then knotting said threads together while preserving that balance;
   i) stretching the threads of the pressing subassemblies so as to tighten the aforementioned choker knots, then knotting the thread of the first pressing subassembly to the thread of the second traction subassembly, and knotting the thread of the second pressing subassembly to the thread of the first traction subassembly; and
   j) engaging the thread of the guying subassembly through the tendon of the subscapularis muscle from the outside in, and through the tendon of the supraspinatus muscle, from the inside out, then stretching that thread and knotting it with itself.

2. The surgical method according to claim 1, wherein the step of connecting the thread of the guying subassembly to the humeral diaphysis comprises the following operations: piercing two holes in the humeral diaphysis pulled back from the fracture area of the tuberosities; and engaging the thread of the guying subassembly through a first of these holes, from the outside toward the inside of a humerus wall, then in the second hole, from the inside toward the outside of the humerus wall.

3. The surgical method according to claim 1, wherein threads of the guying subassembly, traction subassemblies, and pressing subassemblies have different colors.

4. The surgical method according to claim 1, wherein, for each subassembly, the two strands are formed by a single thread, the connection of which at said second ends of said strands is done by the continuation of the single thread.

5. The surgical method according to claim 1, wherein, for each subassembly, the needle is curved.

6. The surgical method according to claim 1, wherein, for each subassembly, the connection of the thread to the corresponding needle is done by stamping, on the thread, a deformable wall defined by the end of the needle intended to be connected to said thread.

7. The surgical method according to claim 1, further comprising using a third traction subassembly, the thread of which is capable of being placed through at least one of the greater tuberosity of the humerus and the tendon of the supraspinous muscle, using a choker knot.

8. The surgical method according to claim 1, further comprising using a second guying subassembly, the thread of which is capable of being engaged through the tendon of the supraspinatus muscle, from the outside in, and through the tendon of the infraspinatus muscle, from the inside out, and to be knotted with itself.

* * * * *